(12) United States Patent
Anderson, III et al.

(10) Patent No.: US 6,376,253 B1
(45) Date of Patent: Apr. 23, 2002

(54) 13C, 15N, 2H LABELED PROTEINS FOR NMR STRUCTURE DETERMINATIONS AND THEIR PREPARATION

(75) Inventors: Frank Elbert Anderson, III, Gaithersburg; Jonathan Miles Brown, Silver Spring, both of MD (US); Philip Edward Coughlin, Wilmington, DE (US); Steven William Homans, Dundee; Charles Tobias Weller, Fife, both of (GB); Carrie Ann Zimmerman-Wilson, Ellicott City; Eddie James Oliver, Jr., Takoma Park, both of MD (US)

(73) Assignee: Martek Biosciences Corporation, Columbia, MD (US)

( * ) Notice: Subject to any disclaimer, the term of this patent is extended or adjusted under 35 U.S.C. 154(b) by 0 days.

(21) Appl. No.: 09/613,570

(22) Filed: Jul. 10, 2000

Related U.S. Application Data

(60) Division of application No. 09/486,837, filed as application No. PCT/US98/18197 on Sep. 2, 1998, which is a continuation-in-part of application No. 08/921,554, filed on Sep. 2, 1997, now Pat. No. 6,111,066.

(51) Int. Cl.$^7$ .......................... G01N 33/00; G01N 24/08
(52) U.S. Cl. ........................................... 436/86; 436/173
(58) Field of Search ................................... 436/86, 173

(56) References Cited

U.S. PATENT DOCUMENTS

| | | |
|---|---|---|
| 5,168,225 A | 12/1992 | Yamazaki et al. |
| 5,324,658 A | 6/1994 | Cox et al. |
| 5,393,669 A | 2/1995 | Brown |
| 5,627,044 A | 5/1997 | Brown |
| 5,698,401 A | 12/1997 | Fesik et al. |
| 5,804,390 A | 9/1998 | Fesik et al. |
| 5,891,643 A | 4/1999 | Fesik et al. |

FOREIGN PATENT DOCUMENTS

| | | |
|---|---|---|
| JP | 2208579 | 8/1990 |
| JP | 4046143 | 2/1992 |
| WO | 9418339 | 8/1994 |
| WO | 9848264 | 10/1998 |
| WO | 9911589 | 3/1999 |

OTHER PUBLICATIONS

Perutz, M.F. et al., "Structure of Hemoglobin: A Three–Dimensional Fourier Synthesis at 5˙5–Å. Resolution, Obtained by X–ray Analysis," vol. 185, pp. 416–422, *Nature* (Feb. 1960).

LeMaster, D et al., "Preparative–Scale Isolation of Isotopically Labeled Amino Acids," vol. 122, pp. 238–247 *Analytical Bochemistry* (1982).

Kay, L et al., "Four–Dimensional Heteronuclear Triple–Resonance NMR Spectroscopy of Interleukin–1β in Solution," vol. 249 pp. 411–414, *Science* (Jul. 1990).

Driscoll, P et al, "Structure of domain 1 of rat T lymphocyte CD2 antigen," vol. 353, pp. 762–765, *Nature* (Oct. 1991).

Archer, S et al., "Transforming Growth Factor β1: Secondary Structure As Determined by Heteronuclear Magnetic Resonance Spectroscopy," vol. 32, pp. 1164–1171, *Biochemistry* (1993).

Ragnarsson, U, Proteinogenic Amino Acids Labelled with $^{15}$N and/or $^{13}$C for Application in Peptide Synthesis: A Short with a Comprehensive List of Published Derivatives, vol. 3, pp. 149–156, *Journal of Peptide Science* (1995).

Nyasse, B et al. "First Synthesis of a Fully [$^{15}$N,$^{13}$C] Backbone–Labelled Peptide. $^{15}$N NMR Spectrum of Corresponding Leu–Enkephalin," *J. Chem. Soc., Chem. Commun*, pp. 2005–2006 (1994).

Lankiewicz, L. et al., "Synthesis of Amino Acid Derivatives Substituted in the Backbone with Stable Isotopes for Application in Peptide Synthesis," pp. 2503–2510, *J. Chem. Soc., Chem. Commun.* (1994).

Archer, S et al., "Transforming Growth Factor β1: NMR Signal Assignments of the Recombinant Protein Expressed and Isotopically Enriched Using Chinese Hamster Ovary Cells," vol. 32, pp.1152–1163, *Biochemistry* (1993).

Freund, C et al., "Structural and Dynamic Properties of the $F_v$ Fragment and the Single–Chain $F_v$ Fragment of an Antibody in Solution Investigated by Heteronuclear Three–Dimensional NMR Spectroscopy," vol. 33, pp. 3296–3303, *Biochemistry* (1994).

Zhou, H et al., "NMR Studies of the Phosphotransfer Domain of the Histidine Kinase CheA from *Escherichia coli*: Assignments, Secondary Structure, General Fold, and Backbone Dynamics," vol. 34, pp. 13858–13870, *Biochemistry* (1995).

Hansen, A et al., "A Practical Method for Uniform Isotopic Labeling of Recombinant Proteins in Mammalian Cells," vol. 31, No. 51, pp. 12714–12718, *Biochemistry* (1992).

Powers, R. et al., "$^1$H, $^{15}$N, $^{13}$C, and $^{13}$CO Assignments of Human Interleukin–4 Using Three–Dimensional Double– and Triple–Resonance Heteronuclear Magnetic Resonance Spectroscopy," vol. 31, No. 17, pp. 4334–4346, *Biochemistry* (1992).

(List continued on next page.)

*Primary Examiner*—Jon P. Weber
(74) *Attorney, Agent, or Firm*—Rothwell, Figg, Ernst & Manbeck

(57) ABSTRACT

The invention is concerned with determining the three-dimensional structure of biological macromolecules such as proteins. In particular, it is concerned with methods for rapidly determining protein structure by NMR, by providing methods for simplifying NMR spectra using labeled proteins prepared from specifically isotopically labeled amino acids having at least two isotopes of 13C, 15N and 2H in the backbone, and methods for making these labeled proteins, e.g., by cultivation of a microbial culture containing said labeled amino acids.

22 Claims, No Drawings

OTHER PUBLICATIONS

Lustbader, J et al., "Expression of human chorionic gonadatropin uniformly labeled with NMR isotopes in Chinse hamster ovary cells: An advance toward rapid determination of glycoprotein structures," vol. 7, pp. 295–304, *Journal of Biomolecular NMR* (1996).

Weller, C. et al., "Structural and Conformational Analysis of Glycan Moieties in Situ on Isotopically $^{13}$C, $^{15}$N–Enriched Recombinant Human Chorioric Gondatropin," vol. 35, pp. 8815–8823 *Biochemistry* (1996).

Grzesiek, S et al., "$^{13}$C Lime Narrowing by $^2$H Decoupling in $^2$H/$^{13}$C/$^{15}$N–Enriched Proteins, Application to Triple Resonance 4D J Connectivity of Sequential Amides,"*J. Am. Chem. Soc.* 115(9):4369–4370. (1993).

Appelt, K et al., Design of Enzyme Inhibitors Using Iteractive Protein Crysallographic Analysis, *Journal of Medical Chemistry* 34 (7):1925–1934 (1991).

Kent, S.B.H. "Chemical Synthesis of Peptides and Proteins," Ann. Rev. Biochem. 57:957–989 (1988).

13C, 15N, 2H LABELED PROTEINS FOR NMR STRUCTURE DETERMINATIONS AND THEIR PREPARATION

CROSS-REFERENCE TO RELATED APPLICATIONS

This application is a division of U.S. application Ser. No. 09/486,837, filed Mar. 15, 2000, which is a 371 of PCT/US98/18197, filed Sep. 2, 1998, which is a continuation-in-part of U.S. application Ser. No. 08/921,554, filed Sep. 2, 1997, now U.S. Pat No. 6,111,066.

FIELD OF THE INVENTION

This invention is concerned with determining the three-dimensional structure of biological macromolecules, especially proteins. In particular, it is concerned with methods for rapidly determining protein structures by NMR spectroscopy, by providing methods for simplifying NMR spectra using labeled proteins prepared from specifically isotopically labeled amino acids, and the means whereby these labeled proteins and amino acids may be obtained.

BACKGROUND OF THE INVENTION

For many years, there has been intense interest in determining the three-dimensional structures of biological macromolecules, particularly proteins. So called "structure-function" studies have been carried out to determine the structural features of a molecule, or class of molecules, that are important for biological activity. Since the pioneering work of Perutz and coworkers on the structure of hemoglobin (Perutz, M. F. et al., *Nature*, 185:416–22 (1960)) and that of Watson and Crick on DNA in the 1950's (Watson, J. D. and Crick, F. H. C., *Nature*, 171:737 (1953), both of which led to the respective scientists receiving the Nobel Prize, this field has been of major importance in the biological sciences.

More recently, the concept of "rational drug design" has evolved. This strategy for the design of drugs involves determining the three-dimensional structure of an "active part" of a particular biological molecule, such as a protein. Knowing the three-dimensional structure of the active part can enable scientists to design a synthetic analogue of the active part that will block, mimic or enhance the natural biological activity of the molecule. (Appelt, K. et al., *J. Med. Chem.*, 34:1925 (1991)). The biological molecule may, for example, be a receptor, an enzyme, a hormone, or other biologically active molecule. Determining the three-dimensional structures of biological molecules is, therefore, of great practical and commercial significance.

The first technique developed to determine three-dimensional structures was X-ray crystallography. The structures of hemoglobin and DNA were determined using this technique. In X-ray crystallography, a crystal (or fiber) of the material to be examined is bombarded with a beam of X-rays which are refracted by the atoms of the ordered molecules in the crystal. The scattered X-rays are captured on a photographic plate which is then developed using standard techniques. The diffracted X-rays are thus visualized as a series of spots on the plate and from this pattern, the structure of the molecules in the crystal can be determined. For larger molecules, it is frequently necessary to crystallize the material with a heavy ion, such as ruthenium, in order to remove ambiguity due to phase differences.

More recently, a second technique, nuclear magnetic resonance (NMR) spectroscopy, has been developed to determine the three-dimensional structures of biological molecules, particularly proteins. NMR was originally developed in the 1950's and has evolved into a powerful procedure to analyze the structure of small compounds such as those with a molecular weight of ≦1000 Daltons. Briefly, the technique involves placing the material to be examined (usually in a suitable solvent) in a powerful magnetic field and irradiating it with radio frequency (rf) electromagnetic radiation. The nuclei of the various atoms will align themselves with the magnetic field until energized by the rf radiation. They then absorb this resonant energy and re-radiate it at a frequency dependent on i) the type of nucleus and ii) its atomic environment. Moreover, resonant energy can be passed from one nucleus to another, either through bonds or through three-dimensional space, thus giving information about the environment of a particular nucleus and nuclei in its vicinity.

However, it is important to recognize that not all nuclei are NMR active. Indeed, not all isotopes of the same element are active. For example, whereas "ordinary" hydrogen, $^1H$, is NMR active, heavy hydrogen (deuterium), $^2H$, is not active in the same way. Thus, any material that normally contains $^1H$ hydrogen can be rendered "invisible" in the hydrogen NMR spectrum by replacing all the $^1H$ hydrogens with $^2H$. It is for this reason that NMR spectroscopic analyses of water-soluble materials frequently are performed in $^2H_2O$ to eliminate the water signal.

Conversely, "ordinary" carbon, $^{12}C$, is NMR inactive whereas the stable isotope, $^{13}C$, present to about 1% of total carbon in nature, is active. Similarly, while "ordinary" nitrogen, $^{14}N$, is nmr active, it has undesirable properties for NMR and resonates at a different frequency from the stable isotope $^{15}N$, present to about 0.4% of total nitrogen in nature. For small molecules, these low level natural abundances were sufficient to generate the required experimental information, provided that the experiment was conducted with sufficient quantities of material and for a sufficient time.

As advances in hardware and software were made, the size of molecules that could be analyzed by these techniques increased to about 10 kD, the size of a small protein. Thus, the application of NMR spectroscopy to protein structural determinations began only a few years ago. It was quickly realized that this size limit could be raised by substituting the NMR inactive isotopes $^{14}N$ and $^{12}C$ in the protein with the NMR active stable isotopes $^{15}N$ and $^{13}C$.

Over the past few years, labeling proteins with $^{15}N$ and $^{15}N/^{13}C$ has raised the analytical molecular size limit to approximately 15 kD and 40 kD, respectively., More recently, partial deuteration of the protein in addition to $^{13}C$- and $^{15}N$-labeling has increased the size of proteins and protein complexes still further, to approximately 60–70 kD. See Shan et al., *J. Am. Chem.Soc.*, 118:6570–6579 (1996) and references cited therein.

Isotopic substitution is usually accomplished by growing a bacterium or yeast, transformed by genetic engineering to produce the protein of choice, in a growth medium containing $^{13}C$-, $^{15}N$- and/or $^2H$-labeled substrates. In practice, bacterial growth media usually consist of $^{13}C$-labeled glucose and/or $^{15}N$-labeled ammonium salts dissolved in $D_2O$ where necessary. Kay, L. et al., *Science*, 249:411 (1990) and references therein and Bax, A., *J. Am. Chem. Soc.*, 115, 4369 (1993). More recently, isotopically labeled media especially adapted for the labeling of bacterially produced macromolecules have been described. See U.S. Pat. No. 5,324,658.

The goal of these methods has been to achieve universal and/or random isotopic enrichment of all of the amino acids of the protein. By contrast, some workers have described methods whereby certain residues can be relatively enriched in $^1$H, $^2$H, $^{13}$C and $^{15}$N. For example, Kay et al., *J. Mol. Biol.*, 263, 627–636 (1996) and Kay et al., *J. Am. Chem. Soc.*, 119, 7599–7600 (1997) have described methods whereby isoleucine, alanine, valine and leucine residues in a protein may be labeled with $^2$H, $^{13}$C and $^{15}$N, but specifically labeled with $^1$H at the terminal methyl position. In this way, study of the proton-proton interactions between some of the hydrophobic amino acids may be facilitated. Similarly, a cell-free system has been described by Yokoyama et al., *J. Biomol. NMR*, 6(2), 129–134 (1995)., wherein a transcription-translation system derived from *E. coli* was used to express human Ha-Ras protein incorporating $^{15}$N serine and/or aspartic acid.

These methods are important, in that they provide additional means for interpreting the complex spectra obtained from proteins. However, it should be noted that the Kay et al. methods are limited to the aliphatic amino acids described above. By contrast, the method described by Yokoyama will facilitate the selective enrichment of any amino acid, but is limited to those proteins that can be expressed in a cell-free system. Glycoproteins, for example, may not be expressed in this system.

Techniques for producing isotopically labeled proteins and macromolecules, such as glycoproteins, in mammalian or insect cells have been described. See U.S. Pat. Nos. 5,393,669 and 5,627,044; Weller, C. T., *Biochem.*, 35, 8815–23 (1996) and Lustbader, J. W., *J. Biomol. NMR*, 7, 295–304 (1996). Weller et al. applied these techniques to the determination of the structure of a glycoprotein including its glycosyl sidechain.

While the above techniques represent remarkable advances in this field, they each suffer from certain disadvantages. For example, all are time-consuming. In X-ray crystallographic methods, crystals can take years to form before the experiment even starts. In NMR spectroscopy, although the protein sample may be used immediately in the NMR experiment, processing the data obtained, i.e., analyzing which signal comes from which set of which atoms (the "assignments"), may also take years. Modern drug discovery research depends heavily on knowledge of the structures of biologically active macromolecules. This research would benefit substantially from enhancements in the capabilities and speed of three-dimensional structural analyses of proteins and other macromolecules.

In the past few years, growth in discovering alternative, rapid methods for the identification of candidate drugs has occurred. Genomic techniques, using rapid DNA sequencing methods and computer assisted homology identification, have enabled the rapid identification of target proteins as potential drug candidates. O'Brien, C., *Nature*, 385 (6616):472 (1997). Once identified, a target protein can be quickly produced using modern recombinant technology. Combinatorial chemistry, wherein large numbers of chemical compounds are simultaneously synthesized on plastic plates, frequently by robots, has revolutionized the synthesis of drug candidates, with tens of thousands of compounds ("libraries") able to be synthesized in a few months. See Gordon, F. M. et al., *J. Mol. Chem.*, 37(10), 1385–1401 (1994). The library is then "screened" by allowing each member of the library to come into contact with the target protein. Those that bind are identified, and similar compounds are synthesized and screened. The whole process continues in an iterative manner until a drug candidate of suitably high binding affinity has been identified. One variation of this screening strategy has recently been published by Fesik et al., *Science*, 274, 1531–34 (1996), wherein the screening of the libraries takes place using NMR against an isotopically labeled protein and the binding is detected from perturbations in the NMR spectrum.

Prior knowledge of the three-dimensional structure of a target protein can enable the design of a "focused" combinatorial library, thereby increasing the likelihood of finding potential drug candidates that interact with the biological molecule of interest. However, whereas genomic and combinatorial chemistry each can be performed in months, known methods for protein structural determinations usually take much longer. Therefore, there is a need for methods to increase the speed with which high resolution structures of proteins, including those that are the targets of potential drug candidates, may be determined.

SUMMARY OF THE INVENTION

The present invention provides novel labeled proteins that are isotopically labeled in the backbone structure, but not in the amino acid side chains. The invention also provides novel cell culture media that contain one or more amino acids isotopically labeled in the backbone structure but not in the side chain, and methods for making a labeled protein by cultivating a protein-producing cell culture on such a culture medium.

In another aspect, the invention provides a method for determining the three-dimensional structure of a protein wherein at least one of the amino acids in the protein is specifically labeled in its backbone but not its side chain with any combination of the NMR isotopes $^2$H, $^{13}$C and $^{15}$N.

In yet another aspect of the present invention, a method is provided for rapidly assigning the signals in the NMR spectrum of a protein wherein at least one of the amino acids in the protein is specifically labeled in its backbone, but not its side chain with any combination of the NMR isotopes $^2$H, $^{13}$C and $^{15}$N.

In preferred embodiments of these various aspects of the invention, the amino acids contained in the culture media and incorporated into the protein structure are labeled in the backbone with $^{13}$C and $^{15}$N and optionally with $^2$H.

DETAILED DESCRIPTION OF THE INVENTION

The invention provides a means for rapidly determining the three-dimensional structure of proteins by NMR. As described in further detail below, this improvement in NMR spectroscopic techniques is accomplished by i) increasing the resolution of key signals in the NMR spectrum and ii) eliminating the splitting of the key signals by an adjacent NMR active nucleus. These effects are accomplished by specifically isotopically labeling at least one of the amino acids utilized in the synthesis of the protein with only those atoms that the analyst wishes to detect in the NMR spectrum, so that all other atoms, including those adjacent to the key nuclei, are unlabeled. This approach is a departure from current NMR labeling techniques wherein the goal has been to prepare proteins in a universally labeled form.

Proteins containing specifically labeled amino acids can be chemically synthesized or expressed by bacteria, yeast or mammalian or insect cells or in cell-free systems, as described by Yokoyama et al. The labeled proteins preferably comprise at least about 50 amino acid residues. The compositions and methods of the invention may advantageously be employed in connection with proteins having molecular masses of at least about 5 kD.

If bacterial or yeast expression is desired, then the medium should contain all of the amino acids necessary for protein biosynthesis in the desired specifically labeled form to prevent non-specific labeling. Notwithstanding the provisions of substantially all amino acids in specifically labeled form, isotope shuffling may still occur with bacteria or yeast grown in such a medium. Accordingly, proteins containing specifically isotopically labeled amino acids are preferably expressed either in a cell-free system or in mammalian or insect cells grown in a medium containing the amino acids required for protein biosynthesis. It is well known that nearly all naturally occurring amino acids cannot be synthesized by mammalian or insect cells, therefore, isotope shuffling will be at a minimum in such cells. The amino acid compositions for insect and mammalian cell culture media are well known. Such media are described in U.S. Pat. Nos. 5,393,669 and 5,627,044, the is disclosures of which are incorporated herein by reference. Generally, all twenty essential amino acids are present in such media, and in accordance with the present invention, any or all such amino acids may be specifically isotopically labeled.

The labeled amino acids of the target protein are labeled at specific positions with any combination of the NMR isotopes $^2H$, $^{13}C$ and $^{15}N$, such that only those atoms desired to be detectable in the spectrum are NMR active. It will be recognized by those skilled in the art that a key set of identifications required in elucidating protein structure by NMR is obtained from the assignment of signals from the backbone of the protein, i.e., in the signals between the α-carbon of a given amino acid and the amino protons of the same and adjacent residues in the protein sequence. Grzesiek, S. and Bax, A. J., *J. Magn. Reson.*, vol. 96:432–440 (1992). In the Grzesiek et al. experiment (the "HNCA experiment"), less than optimal sensitivity and resolution were achieved due to the influence of neighboring atoms whose presence is not essential for background structural assignments, but which nevertheless were detected due to the universal labeling strategies employed. These complications are reduced by employing only specifically labeled amino acids in accordance with this invention.

In the instant invention, the amino acids of the target protein are advantageously labeled at the α-amino group with $^{15}N$ and at the C-carbonyl and the α-carbon with $^{13}C$, while the side chains are left unlabeled. In this way, the signals from the C-carbonyl and the α-carbon are uncoupled from each other using conventional NMR techniques. Importantly, the signal from the α-carbon is not split into two parts by the adjacent β-carbon atom when that carbon is in the inactive, $^{12}C$ form. This approach contrasts with the method described by Matsuo et al., *J. Magn. Reson.*, 113, 91–96 (1996), which uses a selective radio-frequency field to decouple the β-carbon resonances. This method lacks generality, particularly, for serine residues, where the α-carbon and the β-carbon resonances are insufficiently resolved.

In a particularly preferred aspect of the invention, all of the amino acids of the target protein are not only labeled at the α-amino group with $^{15}N$ and at the C-carbonyl and the α-carbon with $^{13}C$, but are also deuterated at the α-carbon, the side chains being left unlabeled. In this way, in addition to the above advantages, the linewidth of the signals from each α-carbon is significantly narrowed because the carbon nucleus is no longer efficiently relaxed by an attached proton. This decrease in linewidth significantly increases the resolution of the distinct signals from each amino acid residue (Grzesiek et al., *J. Am. Chem. Soc.*, 115, 4369–4370 (1993)).

In a further preferred aspect of this invention, all of the amino acids of the target protein are not only labeled at the α-amino group with $^{15}N$ and at the C-carbonyl and the α-carbon with $^{13}C$, but are also partially protonated at the α-carbon. This approach preserves the advantage of line-narrowing mentioned in the previous paragraph, as well as permits the application of experiments that involve protonation at the α-carbon. These experiments include those described for determining long-range structure in macromolcules, which experiments exploit the presence of residual dipolar couplings between atoms such as $^{13}C$ and $^1H$ in dilute liquid crystalline solutions. (Tjandra and Bax, Science 278, 1111–1114 (1997)) The angular information derived from these experiments may be used for determining the structures of large proteins (<40 kDa). The present invention thus may be used in connection with these experiments to restrict the dipolar coupling information to N—H and Cα—H spin pairs, which greatly simplifies the relevant NMR spectra.

In this preferred aspect of the invention, the amino acids are deuterated at the α-carbon to a level of about 30–70% in a preferred embodiment, about 40–60% in a more preferred embodiment, and about 50% in a most preferred embodiment.

Amino acids have been chemically synthesized in unlabeled forms by various means, and some have been synthesized in specifically isotopically labeled forms. See, e.g., Martin, *Isotopes Environ. Health Stud.*, 32:15 (1996); Schmidt, *Isotopes Environ. Health Stud.*, 31:161 (1995). Ragnarsson et al., *J. Chem. Soc. Perkin Trans* 1, 2503 (1994) synthesized BOC labeled forms of the following amino acids: 1,2-$^{13}C_2$, $^{15}N$ Ala, Phe, Leu, and Tyr; 1,2-$^{13}C_2$, 3, 3, 3-$^2H_3$, $^{15}N$ Ala; 1,2-$^{13}C_2$, 3, 3-$^2H_2$, $^{15}N$ Phe; 3, 3, 3-$^2H_3$ Ala. Ragnarsson, *J. Chem. Soc. Chem. Commun.*, 935 (1996) also synthesized BOC labeled 1,2-$^{13}C_2$, 2-$^2H$, $^{15}N$ Ala, Leu and Phe; and 1,2-$^{13}C_2$, 2,2-$^2H_2$, $^{15}N$ Gly which were partly used for conformational studies of the pentapeptide, Leu-Enkephalin (*Biopolymers*, 41:591 (1997)). Unkefer (*J. Lab. Cpd. Radiopharm.*, 38:239 (1996)) synthesized $^{15}N$ labeled Ala, Val, Leu, and Phe as well as 1-$^{13}C$, $^{15}N$ Val. However, as noted above, mammalian cell media require all twenty amino acids for cell growth. In accordance with the present invention, methods for synthesizing all twenty amino acids in specifically labeled form and culture media containing all or any combination of such amino acids are provided.

Specifically isotopically labeled amino acids may be synthesized by asymmetric synthesis from an appropriately isotopically labeled precursor. Glycine, specifically labeled with any combination of $^{13}C$ and $^{15}N$, is readily available commercially. Preferably, therefore, the amino acids are synthesized using glycine, isotopically labeled as required, as a precursor.

Methods for synthesizing amino acids from glycine have been described which may be used in accordance with the present invention (Duthaler, *Tetrahedron*, 50:1539 (1994); Schöllkopf, *Topics Curr. Chem.*, 109:65 (1983); Oppolzer, *Tett. Letts.*, 30:6009 (1989); *Helvetica Chimica Acta*, 77:2363 (1994); *Helvetica Chimica Acta*, 75:1965 (1992)).

In one aspect of the invention, $^{13}C_2$, $^{15}N$-glycine is first esterified with a suitable alcohol, such as methanol, ethanol or isopropanol, to give the corresponding ester.

The amino group of the glycine ester may be protected by procedures known in the art. See Green, *Protective Groups in Organic Synthesis*, Wiley, N.Y. (1991). Schiff bases (Stork, *J. Org. Chem.*, 41:3491 (1976)) are preferred for protection with the diphenyl ketimine (O'Donnell, *J. Org. Chem.*, 47:2663 (1982)) or bis(methylsulfanyl) imine (Hoppe, *Liebigs Ann. Chem.*, 1979, 2066) being particularly preferred. Introducing the protecting group may be accomplished by reacting the glycine ester with the corresponding aryl imine for the diphenyl ketimine protecting group, or by reacting the glycine ester with carbon disulfide and methyl iodide for the bis(methylsulfanyl) imine protecting group.

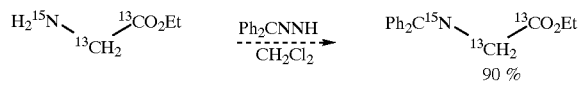

As described above, in a particularly preferred aspect of the invention, the amino acids in the expression medium are deuterated at the α-carbon. If deuterated amino acids are required, then the doubly protected glycine derivative obtained above is deuterated at the α-carbon by treating it with a base in a deuteronic solvent, such as sodium carbonate in $D_2O$ (Ragnarsson, *J. Chem. Soc. Chem. Commun.*, 935 (1996)). To minimize loss of material due to hydrolysis of the ester function, the deuteration is preferably accomplished by treating the doubly protected glycine derivative with a catalytic amount of sodium in an anhydrous deuteronic solvent such as deuteromethanol (MeOD) or deuteroethanol (EtOD).

The required backbone labeled amino acids can now be synthesized from the doubly protected glycine derivative or, preferably, its deuterated analogue, by introducing the characteristic sidechain in a stereospecific manner to preserve the L-configuration at the α-carbon chiral center Methods for such chiral syntheses are known to those skilled in the art. They involve reacting the glycine derivative with a chiral molecule, called a "chiral auxiliary," which directs the subsequent incorporation of the amino acid sidechain in a chiral manner (March, J., *Advanced Organic Chemistry*, 4th ed., Wiley, N.Y., p. 118, 1992).

In a particularly preferred aspect of the invention, the deuterated glycine analogue is converted to the chiral "sultam" derivative. See Oppolzer, *J. Chem. Soc. Perkin 1*: 2503 (1996). For example, methyl or ethyl N-[bis(methylthio) methylidene]glycinate or methyl or ethyl N-(diphenyl methylene)glycinate is treated with (2R)-bornane-10,2-sultam or (2S)-bornane-10,2-sultam in the presence of trimethylaluminum or triethylaluminum and a solvent (usually toluene). (2R)-Bornane-10,2-sultam, ethyl N-(diphenyl methylene)glycinate and trimethylaluminum are particularly preferred for forming the L-amino acids.

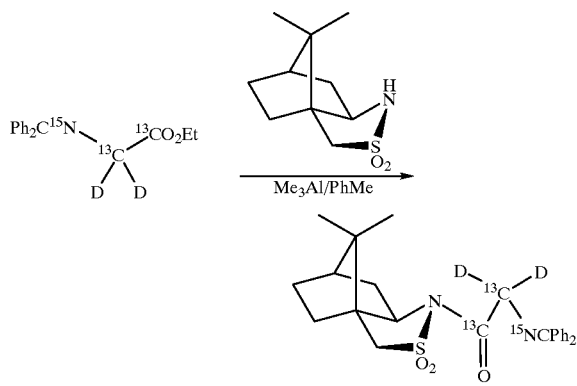

The resulting sultam derivative is then treated with a strong base such as lithium diisopropylamide ("LDA") or n-butyl lithium, in an appropriate solvent such as tetrahydrofuran ("THF"), in the presence of a coordinating solvent such as hexamethylphosphoramide ("HMPA") or N,N-dimethylpropyleneurea ("DMPU") to give the resulting glycine derivative.

To prepare amino acids with simple alkyl sidechains, i.e., alanine, leucine, isoleucine, phenylalanine, methionine, and valine, the derivatized glycine molecule is treated with the appropriate alkyl halide to form the fully protected amino acid. For example, treating the derivatized glycine molecule with benzyl iodide leads to the formation of protected phenylalanine. A list of alkyl halides and corresponding amino acids is provided in Table 1.

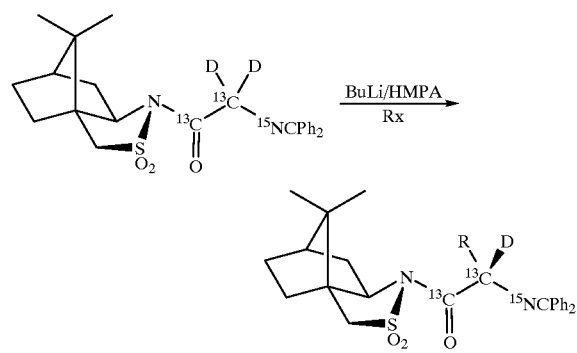

TABLE 1

| Alanine | Me—I |
|---|---|
| Isoleucine | ![isobutyl iodide] |
| Leucine | ![isobutyl iodide] |
| Methionine | MeS-CH2CH2-I |
| Phenylalanine | Ph-CH2-I |

TABLE 1-continued

Valine

The fully protected amino acid thus prepared may be unblocked by a variety of means. The preferred method is a simple two-step procedure consisting of treating the protected amino acid with aqueous acid to remove the imine protecting group, followed by treating the amino acid with an aqueous base to remove the sultam group. In principle, any combination of an aqueous acid and base can be employed, but dilute HCL followed by dilute LiOH is preferred. The liberated, specifically isotopically labeled amino acid may then be further purified by, for instance, ion exchange chromatography.

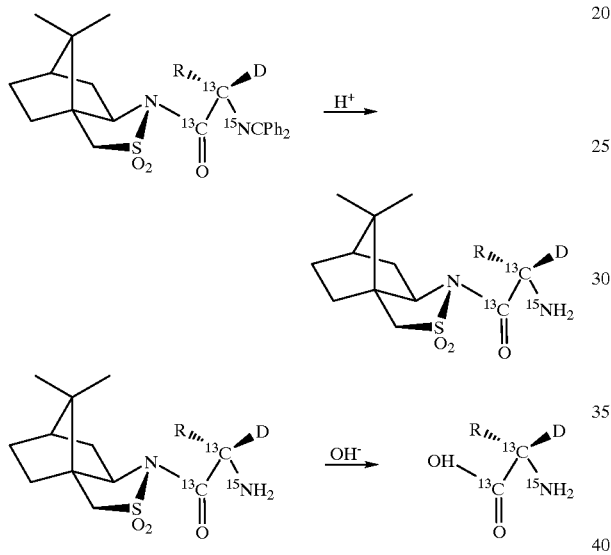

To prepare aspartic acid, glutamic acid, tyrosine, histidine and tryptophan, the functional groups present in the sidechains are advantageously protected prior to reaction with the derivatized glycine molecule. Preferably, the derivatized glycine molecule is treated with a previously protected alkyl halide. For example, aspartic and glutamic acid may be prepared via the commercially available tert-butyl bromoacetate (Oppolzer, *Helvetica Chimica Acta,* 77:2363 (1994)) and methyl acrylate (Schollkopf, *Synthesis,* 737 (1986)), respectively. The alkyl ester protecting group is removed by treating the glycine anion with acid during the two-step unblocking procedure described above to give the desired amino acid.

Similarly, tyrosine may be prepared via the commercially available 4-benzyloxybenzyl or 4-methoxybenzyl chloride. The benzyl or methyl protecting group may be removed prior to the two-step unblocking procedure by, for instance, treating the derivatized glycine molecule with trimethyl silyl iodide in a suitable solvent such as dichloromethane.

Protected sidechain precursors for histidine and tryptophan may be prepared, for example, by the reaction shown in Table 2. For the preparation of the histidine precursor, commercially available 4-hydroxymethyl imidazole hydrochloride is protected at the ring amino nitrogen by a suitable protecting group such as t-boc, F-moc, tosyl, etc. The alcohol functional group of the protected molecule is then converted to a suitable leaving group, e.g., the corresponding halide such as bromide, by reacting the alcohol with a suitable brominating agent, such as free bromine, or triphenylphosphine and carbon tetrabromide, in a suitable solvent such as carbon tetrachloride. The protected bromomethylimidazole derivative may then be reacted directly with the derivatized glycine molecule.

Similarly, the required tryptophan precursor may be prepared from commercially available indole-3-carboxaldehyde via protection of the ring nitrogen with a suitable protecting group such as t-boc, F-moc, etc., followed by conversion to the corresponding alcohol by reduction with, for example, sodium borohydride in ethanol, and halogenation as described above. The protected bromomethylindole derivative may then be reacted directly with the derivatized glycine molecule. The production of these heterocyclic halides and corresponding amino acids is illustrated in Table 2.

TABLE 2

Histidine

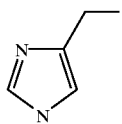
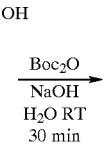
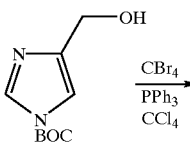

Tryptophan

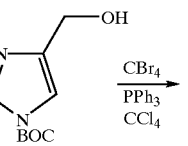
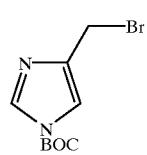
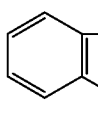

TABLE 2-continued

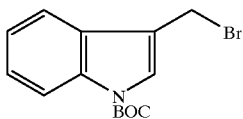

Fully protected tryptophan and histidine may be unblocked by the simple two-step procedure described above as t-boc, F-moc, or tosyl groups may be removed by the acid/base treatment. Again, in principle any combination of an aqueous acid or base can be employed. However, aqueous HCL followed by LiOH is preferred.

Specifically isotopically labeled asparagine and glutamine may be prepared respectively from labeled aspartic acid and glutamic acid prepared above using established techniques. For example, the techniques described in U.S. Pat. Nos. 5,393,669 and 5,627,044 may be used. Alternatively, asparagine and glutamine, and arginine and lysine, can be prepared by treating the derivatized glycine molecule with an alkyl halide carrying a terminal nitrile group. For example, treating the derivatized glycine molecule with 3-bromopropionitrile leads to the formation of the corresponding fully protected nitrile derivative. Following unblocking by the two-step acid/base treatment described above, the resulting amino acid nitrites are converted to the desired amino acids. For example, lysine may be formed by reacting 4-bromobutyronitrile with the derivatized glycine molecule and then reducing the resulting nitrile with a suitable reducing agent such as sodium borohydride and cobalt chloride.

A list of amino acids, corresponding halo-alkyl nitrites and methods for their conversion are provided in Table 3.

TABLE 3

| Asparagine | NC–I | partial hydrolysis |
|---|---|---|
| Arginine | NC~~I | see below |
| Glutamine | NC~~I | partial hydrolysis |
| Lysine | NC~~~I | reduction |

Preferably, arginine is prepared from the nitrile isolated from the two-step unblocking procedure by reducing the nitrile with sodium borohydride and cobalt chloride, followed by treating the resulting ornithine with O-methylisourea tosylate. The O-methylisourea tosylate compound is prepared from urea treated with methyl tosylate in the presence of basic copper II carbonate, followed by treatment with sodium sulfhydride (Kurtz, *J. Biol. Chem.*, 180:1259 (1949)).

The remaining specifically isotopically labeled amino acids required for a specifically labeled mammalian or insect cell medium, i.e., serine, cysteine and threonine, may be prepared, for example, by the enzymatic procedures described in U.S. Pat. Nos. 5,393,669 and 5,627,044 and the references cited therein using $^{13}C_2$, $^{15}N$ glycine and/or $^2H_2$, $^{13}C$, $^{15}N$ glycine as a precursor.

The specifically isotopically. labeled amino acids thus prepared may be incorporated into a mammalian or insect cell medium individually or in any combination so that the protein expressed by the cells growing in the medium may be specifically labeled at the amino acid residues of choice. The composition and use of such medium for bacterial, yeast, mammalian and insect cell lines are well known. The compositions described in U.S. Pat. No. 5,324,658 and in U.S. Pat. Nos. 5,393,669 and 5,627,044 may advantageously be used for the media of this invention.

NMR analysis of the specifically labeled protein thus produced may be used to interpret NMR data from the same protein separately obtained in universally labeled form and thereby expedite the determination of the structure of the protein. For instance, application of the HNCA experiment to a specifically labeled protein will enable the maximum sensitivity and resolution to be obtained for the determination of the protein backbone resonance assignments. The Cα resonance for each amino acid residue will exhibit a correlation with the amide nitrogen atom of the same residue via the one-bond Cαi-Ni coupling, which is then transferred to the amide proton using another transfer via the one-bond Ni-Hi coupling. In addition, certain residues will exhibit a two-bond Cαi-1-(Ci-1)-Ni correlation to the previous residue in such cases where this two-bond coupling is of sufficient magnitude. These latter data can be complemented by data from an experiment known as HN(CO)CA which exhibits exclusively all such two-bond correlations due to transfer via the intervening carbonyl carbon. This latter experiment also shares the advantages gained by the HNCA, experiments with respect to selective labeling. Hence, the HNCA and HN(CO)CA experiments combined, can be used sequentially to assign the backbone resonances of proteins with high-sensitivity, and with sufficient resolution to permit automated analysis with computational algorithms.

The invention is illustrated by the following examples which are for illustrative purposes only and in no way limit the scope of the invention.

EXAMPLES

EXAMPLE 1

Synthesis of Ethyl N-(diphenylmethylene)[1,2-$^{13}C_2$, $^{15}N$, 2,2-$^2H_2$]glycinate Under anhydrous conditions, 4M HCL in dioxane (50 ml) was added to a solution of [1,2-$^{13}C_2$, $^{15}N$]glycine (5 g, 66.6 mmol) in ethanol (100 ml) and refluxed for 1 hour. Evaporating the solvent in vacuo and repeating the procedure twice yielded a white crystalline solid. Benzophenone imine (1 eq.) was added to the ethyl glycinate hydrochloride in dry dichloromethane (100 ml) and stirred at room temperature overnight. Solid was filtered off and the solvent removed in vacuo. The resulting ethyl N-(diphenylmethylene)[1,2-$^{13}C_2$, $^{15}N$]glycinate was recrystallized from hexane.

Under anhydrous conditions, sodium metal (198 mg, 8.6 mmol) was added to a solution of ethyl N-(diphenylmethylene)[1,2-$^{13}C_2$, $^{15}N$]glycinate (19.31 g, 71.25 mmol) in freshly distilled deuteroethanol (250 ml, 60 eq). After stirring overnight at room temperature, the reaction was quenched by adding deuteroacetic acid (0.5 g, 8.6 mmol). Removing the solvent in vacuo, resuspending in dichloromethane (100 ml), filtering and evaporating yielded a white crystalline solid. Recrystallizing from hexane/ethyl acetate gave ethyl N-(diphenylmethylene)[1,2-$^{13}C_2$, $^{15}N$, 2,2-$^2H_2$]glycinate (17 g, 87%).

Example 2

Synthesis of (2R)-N-(diphenylmethylene)[1,2-$^{13}C_2$, $^{15}N$, 2,2-$^2H_2$]glycylbornane-10,2-sultam Over 20 minutes, 2 M trimethylaluminum in hexane (40 ml, 1.2 eq) was added to (2R)-bornane-10,2-sultam (15.7 g, 1.1 eq) in toluene (110 ml) at 0° C., then left for 30 minutes. Ethyl N-(diphenylmethylene)[1,2-$^{13}C_2$, $^{15}N$, 2,2-$^2H_2$] glycinate (18.1 g, 66.4 mmol) in toluene (10 ml) was added and the reaction stirred overnight. Heating to 50° C. for 3–4 hours drove the reaction to completion. Workup was effected by cooling the reaction in ice and carefully adding MeOD (20 ml). After 1 hour, $D_2O$ (30 ml) was carefully added. Filtering, extracting with ethyl acetate (2×250 ml), drying over $MgSO_4$ and purifying by silica gel flash chromatography (Hexane: Ethyl Acetate 10:1 to 1:1) gave (2R)-N-(diphenylmethylene)[1,2-$^{13}C_2$, $^{15}N$, 2,2-$^2H_2$]glycylbornane-10,2-sultam (28.7 g, 99% yield) as an orange oil.

Example 3
Synthesis of (1,2-$^{13}C_2$, $^{15}N$, 2-$^2H$) Valine

Under anhydrous conditions, a solution of n-butyl lithium (2.5 M solution in hexane, 5.39 ml, 1.1 eq) was added to a stirred solution of (2R)-N-(diphenylmethylene)[1, 2-$^{13}C_2$, $^{15}N$, 2,2-$^2H_2$]glycylbornane-10,2-sultam (5.4 g, 12.3 mmol) in dry THF (120 ml) at −78° C. After 15 minutes, the resulting solution was treated with HMPA (21.3 ml, 10 eq). After 1 hour, 2-iodopropane (6.12 ml, 5 eq) was added and the temperature raised to −10° C. After 2 days, the reaction was warmed to room temperature and quenched by adding $D_2O$ (50 ml). Extracting with diethyl ether (100 ml), drying, evaporating and purifying by silica gel chromatography (hexane:ethyl acetate 80:20) yielded 4.85 g (82%) of a semi-crystalline oil.

Deprotection was effected by adding 0.1 M HCL (100 ml) to a solution of the oil in THF (100 ml). After 15 minutes, lithium hydroxide (2.11 g, 5 eq) was added and the reaction stirred at room temperature overnight. Removing the solvent in vacuo, extracting with diethyl ether (5×50 ml) then with hexane (50 ml) and purifying the aqueous phase by ion exchange chromatography (Dowex 8×400 H+ resin) gave the title compound (889 mg, 60%) as a white powder.

Example 4
Synthesis of (1,2-$^{13}C_2$, $^{15}N$, 2-$^2H$) Phenylalanine

A solution of n-butyl lithium (2.5 M soln. in hexane, 10 ml, 1.6 eq) was added to a stirred solution of (2R)-N-(diphenylmethylene)[1,2-$^{13}C_2$, $^{15}N$, 2,2-$^2H_2$]glycylbornane-10,2-sultam (4.32 g, 9.8 mmol) in dry THF (50 ml) at −78° C. After 15 minutes, the resulting solution was treated with HMPA (13 ml, 7 eq) and the temperature raised to −50° C. After 1 hour, benzyl iodide (11.6 g, 5 eq) in THF (50 ml) was added. After 1 hour, the reaction was warmed to room temperature and quenched by adding water (50 ml). Extracting with diethyl ether (5×100 ml), washing with water, drying, and evaporating yielded an oil which was immediately deprotected.

Deprotection was effected by adding 0.2 M HCL (160 ml) to a solution of the oil in THF (160 ml). After 15 minutes, lithium hydroxide (6.71 g, 10 eq) was added and the reaction stirred at room temperature overnight. Removing the solvent in vacuo, extracting with diethyl ether (5×50 ml) then with hexane (50 ml), and purifying the aqueous phase by ion exchange chromatography (Dowex 8×400 H+ resin) gave the title compound (1.2 g, 45%) as a white powder.

Example 5
Synthesis of (1,2-$^{13}C_2$, $^{15}N$) Alanine

A solution of n-butyl lithium (2.5 M soln in hexane, 2.8 ml, 1.1 eq) was added to a stirred solution of (2R)-N-(diphenylmethylene)[1,2-$^{13}C_2$, $^{15}N$]glycylbornane-10,2-sultam (2.77 g, 6.3 mmol) in dry THF (63 ml) at −78° C. After 15 minutes, the resulting solution was treated with HMPA (11 ml, 10 eq). After 1 hour, methyl iodide (2 ml, 5 eq) was added, the reaction temperature raised to −10° C., stirred overnight, then quenched by adding water (20 ml). Extracting with diethyl ether (5×20 ml), washing with water, drying ($MgSO_4$), evaporating and purifying by silica gel chromatography (hexane:ethyl acetate 80:20) yielded 2.34 g (82%) of a yellow crystalline solid.

Deprotection was effected by adding 0.2 M HCL (60 ml) to a solution of the crystals in THF (70 ml). After 15 minutes, lithium hydroxide (2.17 g, 10 eq) was added and the reaction stirred at room temperature overnight. Removing the solvent in vacuo, extracting with diethyl ether (5×50 ml) and purifying the aqueous phase by ion exchange chromatography (Dowex 8×400 H+ resin) gave the title compound (395 mg, 68%) as a white powder.

Example 6
NMR Analysis of Specifically Labeled Phenylalanine

Backbone labeled (>95% $^{13}C$, $^{15}N$, >90% $^2H$) Phe (20 mg) was dissolved in 10 ml saturated $NaHCO_3$, to which was added 5 mole equivalents of acetic anhydride over a period of two hours. Following desalting on a mixed-bed anion and cation exchange resin, the sample was prepared for NMR studies by dissolution in 700 ml $H_2O/D_2O$ (95:5 v/v). Two-dimensional HNCA spectra were acquired with deuterium decoupling on said acylated derivative of backbone-labeled Phe versus the acylated derivative of uniformly triple (>95% $^{13}C$, $^{15}N$, 50% $^2H$) labeled Phe.

Example 7

The acylated derivative of backbone ($^{13}C$, $^{15}N$) labeled and uniformly $^2H$ enriched Phe was dissolved in 700 ul glycerol-d7/$H_2O$ (85% v/v) to a final concentration of 1 mM. A sample of the acylated derivative of uniformly ($^{13}C$, $^{15}N$, $^2H$) Phe was similarly prepared. Two-dimensional HNCA spectra with $^2H$ decoupling were acquired identically on these samples at 0° C. At this temperature, the rotational correlation time of the molecule (~18 ns) and hence resonance linewidths equaled that expected for a ~40 kDa protein.

Example 8
Synthesis of (2R)-N-(diphenylmethylene)[1,2-$^{13}C_2$, $^{15}N$, 2-$^1H$, 2-$^2H$]glycylbornane-10,2-sultam Over 20 minutes, 2 M trimethylaluminium in hexane (10.55 ml, 1.0 eq) was added to (2R)-bornane-10,2-sultam (6.11 g, 1.02 eq) in toluene (50 ml) at 0° C., then left for 30 minutes. Ethyl N-(diphenylmethylene)[1,2-$^{13}C_2$, $^{15}N$] glycinate (6.11 g, 22.8 mmol) in toluene (17 ml) was added and the reaction stirred overnight. Heating to 60° C. for 4–6 hours drove the reaction to completion. Workup was effected by cooling the reaction in ice and carefully adding MeOD (9.1 ml). After 1 hour, $D_2O$ (10.1 ml) was carefully added. Filtering, extracting with ethyl acetate (2×250 ml), and drying over $NaSO_4$ gave (2R)-N-(diphenylmethylene)[1,2-$^{13}C_2$, $^{15}N$, 2-$^1H$, 2-$^2H$]glycylbornane-10,2-sultam (9.9 g, 96% yield) as an orange foam.

Example 9
Synthesis of (1,2-$^{13}C_2$, $^{15}N$, 50% 2-$^2H$) Valine

Under anhydrous conditions, a solution of n-butyl lithium (2.5 M soln in hexane, 5.5 ml, 1.1 eq) was added to a stirred solution of (2R)-N-(diphenylmethylene)(1,2-$^{13}C_2$, $^{15}N$, 2-$^1H$, 2-$^2H$]glycylbornane-10,2-sultam (5.49 g, 12.6 mmol) in dry THF (100 ml) at −78° C. After 15 minutes, the resulting solution was treated with HMPA (21.3 ml, 10 eq). After 1 hour, 2-iodopropane (6.12 ml, 5 eq) was added and the reaction was warmed to room temperature overnight and quenched by adding D$_2$O (2.2 ml). Extraction with diethyl ether (100 ml), drying and evaporation yielded 6.01 g (87.4%) of a white crystalline solid.

Deprotection (of 2.74 g, 5.74 mmol) was effected by adding 1 M HCL (9.06 ml) to a solution of the solid in THF (150 ml) and water (60 ml). After 15 minutes, lithium hydroxide (0.88 g, 3.65 eq) was added and the reaction stirred at room temperature overnight. Removing the solvent in vacuo, extracting with diethyl ether (5×50 ml), then with hexane (50 ml), and purifying the aqueous phase by ion exchange chromatography (Dowex 8×400 H+ resin) gave the title compound (560 mg, 83%) as a white powder.

Example 10
Synthesis of (1,2-$^{13}$C$_2$, $^{15}$N, 50% 2-$^2$H) Phenylalanine

A solution of n-butyl lithium (2.5 M soln. in hexane, 5.77 ml, 1.1 eq) was added to a stirred solution of (2R)-N-(diphenylmethylene)[1,2-$^{13}$C$_2$, $^{15}$N, 2-$^1$H, 2-$^2$H] glycylbornane-10,2-sultam (5:77 g, 13.24 mmol) in dry THF (200 ml) at −78° C. After 15 minutes, the resulting solution was treated with HMPA (22.7 ml, 10 eq). After 1 hour, benzyl bromide (7.87 ml, 5 eq) was added. The reaction was warmed to room temperature overnight and quenched by adding D$_2$O (2.36 ml). Extracting with diethyl ether (5×100 ml), washing with water, drying, and evaporating yielded an oil which was immediately deprotected.

Deprotection was effected by adding 1 M HCL (10.93 ml) to a solution of the oil in THF (72.8 ml) and water (72.8 ml). After 15 minutes, lithium hydroxide (1.07 g, 4.2 eq) was added and the reaction stirred at room temperature overnight. Removing the solvent in vacuo, extracting with diethyl ether (5×50 ml), then with hexane (50 ml), and purifying the aqueous phase by ion exchange chromatography (Dowex 8×400 H+ resin) gave the title compound (0.24 g, 23%) as a white powder.

Example 11
Synthesis of (1,2-$^{13}$C$_2$, $^{15}$N, 50% 2-$^2$H) Leucine

A solution of n-butyl lithium (2.5 M soln. in hexane, 5.77 ml, 1.1 eq) was added to a stirred solution of (2R)-N-(diphenylmethylene)[1,2-$^{13}$C$_2$, $^{15}$N, 2-$^1$H, 2-$^2$H] glycylbornane-10,2-sultam (5.77 g, 13.24 mmol) in dry THF (200 ml) at −78° C. After 15 minutes, the resulting solution was treated with HMPA (22.74 ml, 10 eq). After 1 hour, 1-iodo-2-methyl propane (12.18 g, 5 eq) was added. The reaction was warmed to room temperature overnight and quenched by adding D$_2$O (2.36 ml). Extraction with diethyl ether (5×100 ml), washing with water, drying, and evaporation yielded a solid (6.49 g, 99.7%) which was immediately deprotected.

Deprotection was effected by adding 1 M HCL (12.1 ml) to a solution of the solid in THF (110 ml) and water (81 ml). After 15 minutes, lithium hydroxide (1.1 g, 3.5 eq) was added and the reaction stirred at room temperature overnight. Removing the solvent in vacuo, extracting with diethyl ether (5×50 ml), then with hexane (50 ml), and purifying the aqueous phase by ion exchange chromatography (Dowex 8×400 H+ resin) gave the title compound (0.976 g, 97%) as a white powder.

Example 12

To one liter of CHO S SFM, serum-free media (Life Technologies), supplied by the manufacturer with amino acids, pyruvate and carbohydrate omitted (Catalog No. 0920261) at 37° C. were added 212 mg (1,2-$^{13}$C$_2$, $^{15}$N, 50% 2-$^2$H)leucine, 162 mg (1,2-$^{13}$C$_2$, $^{15}$N, 50% 2-$^2$H)valine, and 188 mg of backbone labeled (1,2-$^{13}$C$_2$, $^{15}$N, 50% 2-$^2$H) phenylalanine. The remaining unlabeled components were added as follows:

ten milliliters of sodium pyruvate 100× solution from Life Technologies (Catalog No. 11360-070),
3.9 grams of glucose,
20 mg aspartic acid,
31 mg glutamic acid,
57 mg asparagine,
82 mg histidine,
820 mg glutamine,
240 mg proline,
240 mg arginine,
135 mg threonine,
155 mg tyrosine,
60 mg methionine,
21 mg tryptophan,
210 mg isoleucine,
291 mg lysine,
18 mg alanine
17 mg glycine
48 mg serine
81 mg cysteine,
81 mg cystine, and
7.4 mg hydroxyproline.

The components were mixed for ten minutes, sonicated for three one-minute intervals, stirred for ten more minutes, and sterile filtered with a 0.2 m PES Nalgene sterile filter. The filtered mixture was transferred to a Nalge bottle for shipping.

The resulting medium was used to culture a CHO cell line engineered to express human choriogonadotropin ("hCG"). Cells were cultured and the specifically isotopically labeled hCG β-subunit was purified by procedures known in the art.

Example 13

Backbone labeled (Phe, Val, Leu) hCG β-subunit (~2.3 mg) was dissolved in 650 ul 100 mM phosphate buffer, and 50 ul 99.96% D$_2$O was added for the field/frequency lock. Two-dimensional HNCA spectra without deuterium decoupling and with deuterium decoupling were acquired at 45° C. with spectral widths of 3600 Hz and 1200 Hz in the $^1$H and $^{13}$C dimensions, respectively. Totals of 256 transients were acquired for each increment in the $^{13}$C dimension, resulting in total acquisition times of 22 hours.

We claim:
1. A method for determining three-dimensional structure information of a peptidic sequence of 50 or more amino acids, comprising:

(a) providing an isotopically substituted nutrient medium which contains all amino acids required for protein biosynthesis, assimilable sources of carbohydrate, essential minerals and growth factors, wherein at least one species of said amino acids in said nutrient medium contains an isotopic substitution; wherein said isotopic substitution is in the backbone structure but not the side chains of said at least one species of amino acid or in the hydrogen atoms bonded to the α-carbon of said at least one species of amino acid or both; and wherein said isotopic substitution is selected from $^{13}$C; $^{15}$N; $^2$H; $^{13}$C and $^2$H; $^{15}$N and $^2$H; $^{13}$C and $^{15}$N; and $^{13}$C, $^{15}$N and $^2$H; with the proviso that when said at least one species of amino acid is glycine, isotopic substitutions of $^2$H may occur at either or both of the hydrogen atoms bonded to the α-carbon with the proviso that essentially none of the isotopic substitutions are present on the side chains of any amino acid;

(b) cultivating in said isotopically substituted nutrient medium, under protein-producing conditions, a bacterial, yeast, mammalian or insect cell culture capable of producing said peptidic sequence of 50 or more amino acids;

(c) recovering said isotopically substituted peptide sequence of 50 or more amino acids from said nutrient medium; and (d) subjecting said isotopically substituted peptidic sequence of 50 or more amino acids to NMR spectroscopic analysis to determine information about its three-dimensional structure.

2. A method according to claim 1 in which said cell culture is a mammalian or insect cell culture.

3. A method according to claim 2, wherein said isotopically substituted peptidic sequence of 50 or more amino acids contains post-translational modifications.

4. A method according to claim 3, wherein said isotopically substituted peptide sequence of 50 or more amino acids is glycosylated.

5. A method according to claim 1, wherein said isotopically substituted peptidic sequence comprises 145 or more amino acids.

6. A method according to claim 1, wherein the α-amino nitrogen of said at least one species of amino acid is substituted with $^{15}N$ and the α-carbon and carbonyl carbons of said at least one species of amino acid are substituted with $^{13}C$.

7. A method according to claim 1, wherein hydrogen atoms bonded to the α-carbon of said species of amino acid are substituted with substituted with $^2H$.

8. A method according to claim 7, wherein hydrogen atoms bonded to the α-carbon of said species of amino acid are about 30% to about 70% substituted with $^2H$.

9. A method according to claim 7, wherein hydrogen atoms bonded to the α-carbon of said species of amino acid are about 40% to about 60% substituted with $^2H$.

10. A method according to claim 7, wherein hydrogen atoms bonded to the α-carbon of said species of amino acid are about 50% substituted with $^2H$.

11. A method according to claim 1, wherein substantially all of said species of amino acid in said nutrient medium contain said isotopic substitution.

12. A method for determining three-dimensional structure information of a peptidic sequence of 50 or more amino acids, comprising:

(a) providing an isotopically substituted nutrient medium for the cultivation of bacterial, yeast, mammalian or insect cell cultures, which contains all amino acids required for protein biosynthesis, assimilable sources of carbohydrate, essential minerals and growth factors, wherein at least one of said amino acids in said nutrient medium contains an isotopic substitution; wherein said isotopic substitution is in the backbone structure but not the side chains of said at least one amino acid or in hydrogen atoms bonded to the α-carbon of said at least one amino acid or both; and wherein said isotopic substitution is selected from $^{13}C$; $^{15}N$; $^2H$; $^{13}C$ and $^2H$; $^{15}N$ and $^2H$; $^{13}C$ and $^{15}N$; and $^{13}C$, $^{15}N$ and $^2H$; with the proviso that when said at least one amino acid is glycine, isotopic substitutions of $^2H$ may occur on either or both of the hydrogen atoms bonded to the α-carbon and with the proviso that essentially none of the isotopic substitutions are present on the side chains of any amino acid;

(b) cultivating in said isotopically substituted nutrient medium, under protein-producing conditions, a bacterial, yeast, mammalian or insect cell culture capable of producing said peptidic sequence of 50 or more amino acids;

(c) recovering said isotopically substituted peptidic sequence of 50 or more amino acids from said nutrient medium; and (d) subjecting said isotopically substituted peptidic sequence of 50 or more amino acids to NMR spectroscopic analysis to determine information about its three-dimensional structure.

13. A method according to claim 12 in which said cell culture is a mammalian or insect cell culture.

14. A method according to claim 13, wherein said isotopically substituted peptide sequence of 50 or more amino acids contains post-translational modifications.

15. A method according to claim 14, wherein said isotopically substituted peptidic sequence of 50 or more amino acids is glycosylated.

16. A method according to claim 12, wherein said isotopically substituted peptidic sequence comprises 145 or more amino acids.

17. A method according to claim 12, wherein the α-amino nitrogen of said at least one amino acid is substituted with $^{15}N$ and the α-carbon and carbonyl carbon of said at least one amino acid are substituted with $^{13}C$.

18. A method according to claim 12, wherein hydrogen atoms bonded to the α-carbon of said at least one amino acid are substituted with $^2H$.

19. A method according to claim 18, wherein hydrogen atoms bonded to the α-carbon of said at least one amino acid are about 30% to about 70% substituted with $^2H$.

20. A method according to claim 18, wherein hydrogen atoms bonded to the α-carbon of said at least one amino acid are about 40% to about 60% substituted with $^2H$.

21. A method according to claim 18, wherein hydrogen atoms bonded to the α-carbon of said at least one amino acid are about 50% substituted with $^2H$.

22. A method according to claim 12, wherein substantially all of said amino acids in said nutrient medium contain said isotopic substitution.

* * * * *